United States Patent
Dubnack

(10) Patent No.: US 6,312,422 B1
(45) Date of Patent: *Nov. 6, 2001

(54) PROCESS AND ARRANGEMENT FOR MONITORING AND CONTROLLING THE TREATMENT PARAMETERS IN AN OPHTHALMIC TREATMENT DEVICE

(75) Inventor: Steffen Dubnack, Jena (DE)

(73) Assignee: Carl Zeiss Jena GmbH, Jena (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/263,620

(22) Filed: Mar. 5, 1999

(30) Foreign Application Priority Data

Mar. 30, 1998 (DE) .............................................. 198 14 095

(51) Int. Cl.⁷ .................................................... A61B 18/18

(52) U.S. Cl. .................................... 606/4; 606/5; 606/11; 606/12; 606/17; 128/898; 351/200; 351/205; 351/219

(58) Field of Search ................................ 606/4–6, 16, 17, 606/10, 166; 351/205, 214, 216, 219; 128/8–98

(56) References Cited

U.S. PATENT DOCUMENTS

| | | | |
|---|---|---|---|
| 5,098,426 | * 3/1992 | Sklar et al. ............... | 606/5 |
| 5,279,298 | 1/1994 | Flower .................... | 128/633 |
| 5,355,181 | * 10/1994 | Ashizaki et al. ........... | 348/744 |
| 5,423,801 | * 6/1995 | Marshall et al. ............ | 606/5 |
| 5,865,832 | * 2/1999 | Knopp et al. .............. | 606/10 |
| 5,891,131 | * 4/1999 | Rajan et al. ............... | 606/5 |
| 5,895,384 | * 4/1999 | Steiner et al. .............. | 606/5 |
| 5,984,916 | * 11/1999 | Lai ........................ | 606/11 |
| 6,033,396 | * 3/2000 | Huang et al. .............. | 606/5 |

FOREIGN PATENT DOCUMENTS

| | | |
|---|---|---|
| 42 32 021 | 7/1997 | (DE) . |
| 2 252 249 | 8/1992 | (GB) . |
| WO 84 03220 | 8/1984 | (WO) . |
| WO 87 05204 | 9/1987 | (WO) . |
| WO 90 08523 | 8/1990 | (WO) . |

* cited by examiner

Primary Examiner—Linda C. M. Dvorak
Assistant Examiner—Ahmed Farah
(74) Attorney, Agent, or Firm—Reed Smith LLP

(57) ABSTRACT

A process for monitoring and controlling the adjustment of treatment parameters in an ophthalmic treatment device which comprises a radiation source generating at least a treatment beam and, optionally, a target beam and an applicator which is connected with the radiation source via at least one optical element and can be attached to a slip lamp, wherein the following steps are provided: a) the irradiation parameters such as intensity, magnification of the contact lens placed on the eye, radiation dose per unit area, and spot size on the retina are adjusted by the operator at the radiation source; b) first parameters to be adjusted at the applicator are calculated on the basis of patient-related influencing variables such as contact lens magnification and the size of the spot to be realized on the retina, so that a determined spot size and intensity of the treatment beam to be applied can be realized at the treatment site on the retina; and c) parameters adjusted at the applicator are compared with the first parameters by means of a computer and the adjusted parameters are made to coincide with the first parameters representing reference values, and the parameters serving as reference values are realized and maintained constant for the duration of irradiation. An arrangement for carrying out the process employing an ophthalmic treatment device is also disclosed.

17 Claims, 1 Drawing Sheet

PROCESS AND ARRANGEMENT FOR MONITORING AND CONTROLLING THE TREATMENT PARAMETERS IN AN OPHTHALMIC TREATMENT DEVICE

BACKGROUND OF THE INVENTION a) Field of the Invention

The invention is directed to a process and arrangement for monitoring and controlling the treatment parameters in an ophthalmic treatment device, especially for adjusting and monitoring the application of the actual amount of radiation (treatment parameter) to be applied to the specific patient in photodynamic therapy (PDT) of diseased tissue in the fundus of the eye, especially for the treatment of age-related macular degeneration which usually leads to a (progressive) destruction of the central retinal portions with irreversible loss of visual function. In the proliferative form of macular degeneration, a neovascularization which originates in the choroid and destructively grows under and into the retina of the eye is responsible for the course of the disease. Harmful scarring occurs in the end stage.

b) Description of the Related Art

It is known to isolate thromboses and neovascularization in the eye through photodynamic therapy in that a selective and localized treatment of the affected locations and tissue parts of the eye is carried out through photodynamic effects. For targeted implementation of such treatment of diseased tissue, the patient is injected with photosensitizers which selectively concentrate in diseased tissue parts of the eye after a certain period of time and enable effective radiation treatment with laser light of suitable wavelength.

Lasers are preferably used for photosensitization after injection with sensitizers, these lasers emitting a wavelength of adjustable output suitable for exciting the photosensitization, wherein the adjusted output value depends, among other things, on the injected dye and on any opacity which may be present in the eye to be treated.

The light emitted by the laser is coupled into an applicator via suitable optical elements, e.g., light guides, wherein the light is directed onto the portion of the retina of the eye to be treated by means of the applicator. The setting parameters, such as the diameter of the treatment area and the radiation output, are determined and adjusted by the treating physician.

A target beam which assists the physician in orienting the applicator in such a way that a treatment beam can expose the surface to be treated in the eye is generated by a second, substantially weaker laser which emits light of a different wavelength. This target beam is also coupled into the applicator through the optical elements.

Treatments should take into account patient-related parameters such as the size of the area to be treated in the eye, consideration of the influence of any opacity that may be present in the eye of the patient, and maintaining a defined maximum radiation intensity and dye-related parameters (energy flux density). However, in currently used laser systems, only the parameters of output, energy and duration of irradiation can be adjusted in the device. Thus, it is disadvantageous that in order to adapt the actual parameters to be used the physician or user must convert the individual values by means of tables or other means and must guarantee that these values are maintained. This method is a source of human error on the part of the physician or user and can have direct consequences on the success of the treatment.

OBJECT AND SUMMARY OF THE INVENTION

Therefore, it is the primary object of the invention to eliminate these disadvantages of the prior art and to provide a process and an arrangement for monitoring and controlling the treatment parameters in an ophthalmic treatment device by which a photodynamic therapy of diseased tissues in the eye which is extensively free from human error can be achieved and by which a reliable handling and adjustment of these devices is made possible.

According to the invention, this object is met by an ophthalmic process for mounting and controlling the adjustment of treatment parameters in an ophthalmic treatment device which comprises a radiation source generating at least a treatment beam and, optionally, a target beam and an applicator which is connected with the radiation source via at least one optical element, wherein the applicator can be attached to a slit lamp comprising the steps of adjusting, by the operator at the radiation source, the radiation parameters such as intensity, magnification of the contact lens placed on the eye, radiation dose per unit area, and spot size on the retina; calculating first parameters to be adjusted at the applicator on the basis of patient-related influencing variables such as contact lens magnification and the size of the spot to be realized on the retina, so that a determined spot size and intensity of the treatment beam to be applied can be realized at the treatment site on the retina; and comparing the parameters adjusted at the applicator with the first parameters by a computer and making the adjusted parameters coincide with the first parameters representing reference values and the parameters serving as reference values being realized and maintained constant for the duration of the radiation. According to an arrangement, it is made possible to carry out the process in a simple manner in an ophthalmic device, wherein the device comprises a radiation source generating a target beam and a treatment beam and has a computer or a control unit and an applicator which directs the radiation into the eye to be treated and enables observation by the operator. This applicator can be attached to a slit lamp. A laser unit with a target laser and a treatment laser, for example, can be provided as radiation source. The radiation source and the applicator are connected with one another by at least one optical element, for example, a light guide, which transmits the target beam and treatment beam. An information connection is also provided so that radiation parameters and/or other information representing controlling variables can be transmitted between the applicator and the laser unit. This information connection can be constructed in the form of an electrical connection, e.g., in the form of an electrical cable, which can be coupled, e.g., to a part of the applicator at which there is also provided the input of the optical element which is constructed, for example, as a light guide.

During the process, the patient-related and dye-related irradiation parameters such as intensity, magnification of the contact lens used, radiation dose per unit area (energy flux density) and the spot size on the retina are adjusted by the user or operator at the radiation source. Taking into account the influencing variables depending on the patient, such as contact lens magnification and the spot size to be realized on the retina (reference spot size), an appropriate adjustment is carried out by means of a controlling and regulating unit by adjustment means at the applicator so as to achieve a determined, desired intensity and spot size of the treatment beam on the irradiation site in the fundus of the eye. Exactly defined conditions are achieved and maintained during irradiation in that the irradiation parameters adjusted at the applicator are compared with the reference parameters by means of a computer and in that these values are continuously made to correspond to one another and are maintained constant during irradiation.

In this respect, it is advantageous when the intensity of the laser radiation at the irradiation site is compared with the radiation values to be applied and when, in the event of difference between these values, the intensity is maintained constant during irradiation automatically or manually by changing the spot size by means of an optical system provided in the applicator and/or by changing the output of the radiation source. The optical system comprises a beam expansion system and an objective. In order to achieve a high degree of safety for the patient, changes in the adjustment of the spot size are detected automatically by the radiation source by means of the optical system of the applicator and are corrected or the irradiation is interrupted by turning off the laser until the desired (intended) intensity of the radiation used is reestablished. The transmission of the corresponding electric control signals is carried out by the information connection between the radiation source and the applicator, e.g., via an electric cable.

It is further advantageous that the operator is alerted to a deviation of the actual spot size from the intended spot size by optical and/or acoustical signals and the irradiation is interrupted until the correct spot size is realized again. The correct position or deviations therefrom are also indicated through corresponding optical or acoustical signals. All of these optical or acoustical signals are made perceptible to the operator on a display panel or in another suitable manner for a certain period of time or until the actual parameters again coincide with the intended parameters.

The reference time needed for applying the desired radiation dose is determined from the spot size and from the adjusted intensity of the treatment beam, wherein the irradiation is stopped automatically when this reference time is reached. In this way, injury to the eye of the patient through an excessive radiation dose is reliably prevented.

It is likewise advantageous when the intensity applied during the irradiation is integrated over the time period that has already expired, wherein the irradiation is also stopped automatically when the prescribed radiation dose (energy flux density) is achieved and when the integration of the intensity is interrupted during an interruption in the irradiation and a counter recording the lapsed time is stopped. Thus, it is possible to have as many interruptions of different length as desired and it is ensured that the intensity to be applied cannot be exceeded because the laser is turned off automatically when the predetermined radiation dose is reached.

The arrangement is advantageously outfitted with a timer which can be set in any desired way by the operator and with which the time between the injection of the dye and the beginning of irradiation can be set beforehand. This combination also improves the existing interface between user/patient and treatment device and increases patient safety during irradiation and also the changes of a successful treatment.

In the following, the invention will be explained more fully with reference to an embodiment example.

BRIEF DESCRIPTION OF THE DRAWING

The schematic drawing shows a simplified view of an arrangement for carrying out the process.

DESCRIPTION OF THE PREFERRED EMBODIMENTS

Figure 1:
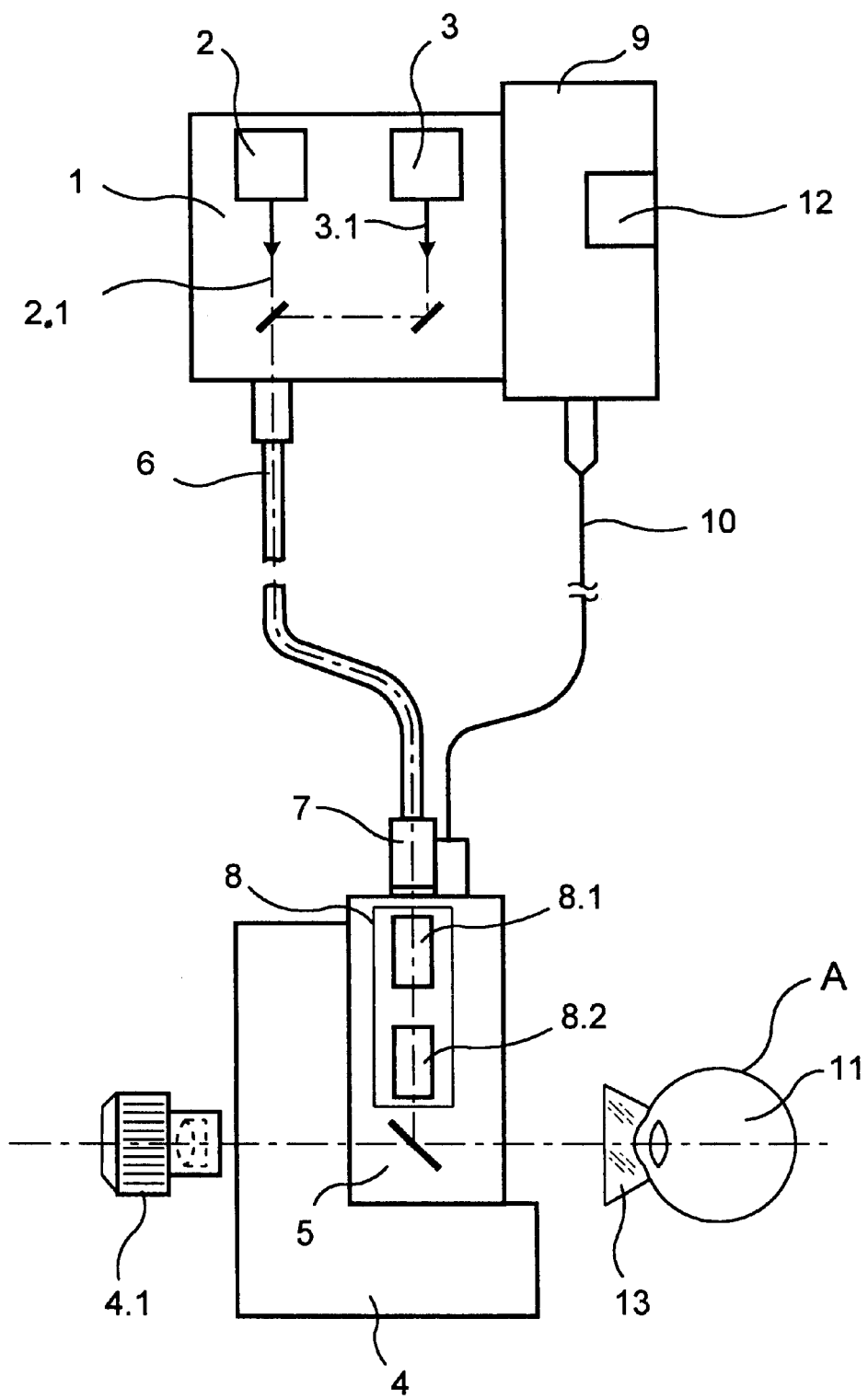

In order to carry out the process for monitoring and controlling the adjustment of treatment parameters in photodynamic therapy of diseased tissue in the interior of the eye A, a treatment device is used which comprises a radiation source 1 generating a treatment beam 3.1 and a target beam 2.1, wherein the radiation source 1 has a target laser 2 and a treatment laser 3 as well as a slit lamp 4 to which can be connected an applicator 5, as it is called. In the coupled state, the slip lamp 4 and applicator 5 form the unit through which the treatment beam 3.1 and target beam 2.1 for irradiation can be directed on or into the eye and by which the treating physician can observe the eye A through observation optics 4.1, wherein a contact lens 13 is placed on the eye A for coupling in the light. The applicator 5 itself is connected with the radiation source 1 by an optical element 6 which guides the light of the target beam 2.1 and the light of the treatment beam 3.1 from the radiation source 1 constructed as laser unit to the applicator 5. A coupler 7 with integrated coupling in optics (not shown) is provided at the applicator 5 for the purpose of coupling the optical element 6. Further, an optical system 8 comprising a beam expansion system 8.1 and an objective 8.2 or only a zoom objective is provided in the applicator 5, wherein the size of the spot and the magnification can be adjusted with the beam expansion system 8.1 and by taking into account the contact lens 13 placed on the eye A of the patient.

According to the process and the work with the treatment device, the treatment parameters such as intensity, the magnification of the contact lens 13 which is placed on the eye A, radiation dose per unit area and the size of the spot are preselected and adjusted at the laser unit 1 by the operator or treating physician. The reference parameters of the device which are to be adjusted at the applicator 5 are calculated on the basis of influencing variables which depend on and are influenced by the patient, e.g., the size of the spot to be realized on the retina, so that the intensity and spot size of the treatment beam which are to be applied for the treatment can be realized at the treatment site on the retina. Irradiation conditions which are always exactly defined are achieved and maintained during the irradiation of the eye A to be treated and are prevented from exceeding or falling below the intensity and/or irradiation dose required for treatment in that the parameters adjusted at the applicator 5 are compared by a computer 9 with the reference parameters for the device to be realized for irradiation, wherein these parameters which represent reference values are brought into line with one another and maintained constant.

The delivered output of the radiation source is determined from the spot size on the retina and from the adjusted intensity of the treatment beam. The treatment period lasts until the preadjusted radiation dose (radiation density per unit area) is reached. The treatment laser 3 is then automatically turned off. During the treatment (irradiation) of the eye A of the patient, the applied intensity is detected and integrated over the irradiation period, wherein the integration (summing) of the intensity is interrupted during interruptions in the treatment. The remaining time necessary for the rest of the irradiation is indicated to the treating physician. It is also possible to record the time during which irradiation of the eye has already been carried out.

In order to realize this in a reliable manner, the intensity of the radiation applied at the treatment site in the fundus 11 of the eye A is compared with the reference intensity to be applied and is also maintained constant automatically if the spot size should change during irradiation. The changing of the spot size is carried out by adjusting the beam expansion system 8.1 which is a component of the optical system 8 arranged in the applicator 5. The changes in the adjustment of the spot size by means of the beam expansion system 8.1 are automatically detected by the radiation source 1. When there are differences between the setting of the spot size at the beam expansion system 8.1 of the applicator 5 and the spot size necessary for irradiation, the treatment laser 3 is automatically turned off in order to reliably prevent incorrect irradiation. The time and the integration of the intensity are likewise stopped. When the intended spot size is readjusted at the applicator, the treatment laser 3 is turned on again and the intensity is integrated again and the time remaining for the irradiation is accordingly further reduced.

At least one connection 10 transmitting information, especially an electrical connection in the form of a cable, is provided for transmitting the necessary signals which serve, among other things, to control the beam expansion system 8.1 or a zoom objective, if any, in the applicator 5 and which represent irradiation parameters or treatment parameters and/or controlling variables. This cable is advantageously arranged at the part of the applicator 5 at which the coupler 7 for the optical element 6 is also located.

Acoustical and/or optical signals are advantageously generated in order to alert the treating physician to deviations between the actual spot size and the intended spot size and to the fact that changes must be carried out in this respect at the treatment device. These acoustical and/or optical signals can, in part, last until the actual spot size is again matched to the necessary spot size manually or automatically. These signals can also only be sent for a certain period of time.

The above-mentioned deviations in the spot size can be indicated in particular by an inverse display on the display panel of the device. The type of deviation from the prescribed position or the direction of the adjustment to be carried out can be meaningfully indicated by arrows. When the correct value is adjusted again, the display returns to normal.

Accordingly, any number of interruptions and any durations of interruption are possible during the treatment, wherein the integration of the intensity is interrupted and the counter or counters 12 counting the time period is/are stopped.

The treatment device can also be provided with a timer (time counter) which is set by the user and, for example, presets the time between the injection of dye and the start of irradiation. Count-down counters are advantageously used for this purpose. When the preallotted time expires, acoustical and/or optical signals announcing the lapsed treatment period are generated at regular intervals. This combination improves in particular the interface between the user/patient and treatment device and increases safety during irradiation of parts of the eye as well as the success of the treatment.

While the foregoing description and drawings represent the preferred embodiments of the present invention, it will be obvious to those skilled in the art that various changes and modifications may be made therein without departing from the true spirit and scope of the present invention.

What is claimed is:

1. A process for monitoring and controlling the adjustment of treatment parameters in an ophthalmic treatment device, which treats a treatment site of an eye which comprises a radiation source generating at least a treatment beam and, optionally, a target beam, and further comprising an applicator which is connected with the radiation source via at least one optical element, wherein the applicator can be attached to a slit lamp, comprising the steps of:

a) adjusting, by the operator patient-dependent irradiation parameters for intended treatment values which set the intensity of a treatment beam, magnification of a contact lens placed on the eye, radiation dose per unit area, and spot size on the retina;

b) calculating reference parameters to be used to adjust the applicator on the basis of the patient-dependent irradiation parameters wherein the calculated reference parameters determine the necessary magnification and irradiation output needed at the applicator to produce the patient-dependent irradiation parameters for the intended treatment values at the treatment site on the retina;

c) applying the treatment beam to the treatment site of the eye;

d) measuring actual parameters for actual magnification and actual irradiation output of the applicator;

e) comparing the reference parameters to be used to adjust the applicator with the actual parameters by a computer; and f) adjusting the actual parameters to continuously coincide with the reference parameters thereby realizing and maintaining the patient-dependent irradiation parameters for the intended treatment values as constant for the duration of irradiation.

2. The process according to claim 1, wherein when there are differences between the patient-dependent irradiation parameters and the actual parameters when the spot size remains constant at the applicator, an output of the radiation source is changed automatically or manually in such a way that the patient-dependent irradiation parameters to be applied are realized again.

3. The process according to claim 1, wherein the optical element is a light guide.

4. The process according to claim 1, wherein the radiation source is a laser unit.

5. The process according to claim 1, wherein an optical system comprising a beam expansion system and an objective is provided in the applicator.

6. The process according to claim 1, wherein an appropriate adjustment of an optical system in the applicator is carried out automatically or manually as a function of the respective spot size and by taking into account the utilized contact lens magnification in order to achieve a desired intensity of the treatment beam at the treatment site on the retina.

7. The process according to claim 1, wherein changes in the adjustment of the spot size at an optical system in the applicator are detected automatically by the radiation source and the irradiation is interrupted by turning off a treatment laser of the radiation source generating the treatment beam until the necessary spot size and the desired intensity of the radiation used is readjusted.

8. The process according to claim 1, wherein the operator is alerted to a deviation of an actual spot size from an intended spot size by acoustical signals.

9. The process according to claim 1, wherein a deviation of the actual spot size from the spot size set by the patient-dependent irradiation parameters is displayed to the operator on a display panel optically or acoustically until the spot size set by the patient-dependent irradiation parameters is realized again.

10. The process according to claim 1, wherein the adjustment of treatment parameters carried out is displayed to the operator optically or acoustically.

11. The process according to claim 1, wherein a reference time needed for applying the desired radiation dose is determined from the adjusted intensity and radiation dose of the treatment beam, and wherein the irradiation is stopped automatically when this reference time expires by a timer recording the time of when the adjusted radiation dose is reached.

12. The process according to claim 1, wherein the intensity of the treatment beam applied during the irradiation is integrated over a time period that expired, wherein during interruption of the irradiation, the integration of the intensity is also interrupted, and a counter recording the time elapsed for irradiation is halted, and wherein the irradiation is stopped when the intended radiation dose is reached.

13. The process according to claim 1, wherein a remaining time needed to reach the radiation dose to be applied is recorded by a counter, and wherein the radiation source is turned off when this remaining time expires.

14. An arrangement for carrying out a process with an ophthalmic device which treats a treatment site of an eye, said process including the steps of:
   a) adjusting, by the operator, patient-dependent irradiation parameters for intended treatment values which set the intensity of a treatment beam, magnification of a contact lens placed on the eye, radiation dose per unit area, and spot size on the retina;
   b) calculating reference parameters to be used to adjust an applicator on the basis of the patient-dependent irradiation parameters wherein the calculated reference parameters determine the necessary magnification and irradiation output needed at the applicator to produce the patient-dependent irradiation parameters for the intended treatment values at the treatment site on the retina;
   c) applying the treatment beam to the treatment site of the eye;
   d) measuring actual parameters for actual magnification and actual irradiation output of the applicator; and
   e) comparing the reference parameters to be used to adjust the applicator with the actual parameters by a computer; and
   f) adjusting the actual parameters to continuously coincide with the reference parameters thereby realizing and maintaining the patient-dependent irradiation parameters for the intended treatment values as constant for the duration of irradiation; wherein said ophthalmic device comprises:
      a radiation source generating at least a treatment beam and, optionally, a target beam, with a control unit or a computer; and
      an applicator which can be attached to slit lamp and which directs the radiation into the eye to be treated and enables observation by the operator; wherein the radiation source and the applicator are connected by an optical element for the transmission of radiation;
      at least one connection transmitting information or controlling variables being provided for the transmission of signals representing the irradiation parameters or controlling variables.

15. The arrangement according to claim 14, wherein the at least one connection is an electrical connection which transmits information or controlling variables and which can be coupled to the part of the applicator at which an input of a light waveguide is also arranged.

16. The arrangement according to claim 15, wherein the at least one electrical connection is a cable which is arranged at the part of the applicator at which an input of the light waveguide is also arranged.

17. The arrangement according to claim 14, wherein there is provided a timer which is set by the operator and by which the time between an injection of a dye and the beginning of irradiation can be set beforehand, wherein the timer alerts the operator to the expiration of the time optically or acoustically.

* * * * *